(12) United States Patent
Emanuel et al.

(10) Patent No.: US 9,717,805 B2
(45) Date of Patent: *Aug. 1, 2017

(54) COMPOSITION AND METHOD FOR MEDICAL IMAGING OR BODY CAVITIES

(71) Applicant: GynaecologIQ B.V., Rotterdam (NL)

(72) Inventors: Mark Hans Emanuel, Aerdenhout (NL); Niek Exalto, Aerdenhout (NL)

(73) Assignee: GynaecologIQ B.V., Rotterdam (NL)

( * ) Notice: Subject to any disclaimer, the term of this patent is extended or adjusted under 35 U.S.C. 154(b) by 70 days.

This patent is subject to a terminal disclaimer.

(21) Appl. No.: 14/663,374

(22) Filed: Mar. 19, 2015

(65) Prior Publication Data

US 2015/0182639 A1    Jul. 2, 2015

Related U.S. Application Data

(62) Division of application No. 11/632,364, filed as application No. PCT/NL2005/000507 on Jul. 14, 2005, now Pat. No. 8,992,887.

(30) Foreign Application Priority Data

Jul. 15, 2004   (EP) .................................... 04077057

(51) Int. Cl.
   *A61K 49/22*   (2006.01)
   *A61K 49/00*   (2006.01)

(52) U.S. Cl.
   CPC .......... *A61K 49/0002* (2013.01); *A61K 49/22* (2013.01); *A61K 49/226* (2013.01)

(58) Field of Classification Search
   CPC ................................ A61K 49/00; A61K 49/22
   See application file for complete search history.

(56) References Cited

U.S. PATENT DOCUMENTS

| | | | |
|---|---|---|---|
| 4,680,175 A | 7/1987 | Estis et al. | |
| 4,681,119 A | 7/1987 | Rasor et al. | |
| 4,985,233 A | 1/1991 | Klaveness et al. | |
| 5,352,434 A * | 10/1994 | Illig ...................... | A61K 49/04 424/709 |
| 5,425,366 A | 6/1995 | Reinhardt et al. | |
| 6,231,513 B1 | 5/2001 | Daum et al. | |
| 6,280,702 B1 * | 8/2001 | Carter .................. | A61K 49/006 424/1.11 |
| 7,727,155 B2 | 6/2010 | De Ziegler | |
| 2003/0206862 A1 | 11/2003 | Gieselmann | |
| 2005/0255039 A1 | 11/2005 | Desai | |
| 2008/0206161 A1 | 8/2008 | Tamarkin et al. | |

FOREIGN PATENT DOCUMENTS

| | | |
|---|---|---|
| EP | 1 793 660 B1 | 6/2007 |
| EP | 1 793 860 B1 | 6/2007 |
| WO | Wo-92/00707 | 1/1992 |
| WO | WO-94/07417 | 4/1994 |
| WO | WO-01/24775 | 4/2001 |
| WO | WO-01/82937 | 11/2001 |
| WO | WO-03/045308 | 6/2003 |
| WO | WO-03/094710 | * 11/2003 |
| WO | WO-2004/073750 | 9/2004 |
| WO | WO-2006/006861 | 1/2006 |
| WO | WO-2007/030002 | 3/2007 |

OTHER PUBLICATIONS

Boudghene, et al. "Assessment of Fallopian tube patency by HyCoSy: comparison of a positive contrast agent with saline solution", Ultrasound Obstet Gynecol (2001), vol. 18, pp. 525-530.
Cellulose—Wikipedia—Dec. 20, 2011, 38 pgs.
Chi-Fishman, et al. "Effects of Systemantic Bolus Viscosity and Volume Changes on Hyoid Movement Kinematics", Dysphagia (2002), pp. 1-17.
Complete info on herbals, vitamins & dietary supplements, RxMed: Pharmaceutical Information—Echovist, Dec. 4, 2013, 4 pgs.
EchoVist—Information Leaflet—A guide to using Echovist (galactose), Dec. 6, 2013.
Emanuel, et al. "First experiences with hysterosalpingo-foam sonography (HyFoSy) for office tubal patency testing", Human Reproduction (2011) vol. 0, No. 0, pp. 1-4.
International Search Report in PCT/NL2005/000507 mailed Oct. 6, 2005.
International Search Report in PCT/NL2010/050679 mailed Apr. 21, 2011.
Killick, "Hysterosalpingo contrast sonography as a screening test for tubal patency in infertile women", Journal of the Royal Society of Medicine (Dec. 1999), vol. 92, pp. 628-631.
MSDS—Methyl—cellulose (2% solution in water) viscosity 3500-5600—ACC# 00966 (1998) 5 pgs.

* cited by examiner

*Primary Examiner* — Michael G Hartley
*Assistant Examiner* — Jagadishwar Samala
(74) *Attorney, Agent, or Firm* — Gilberto M. Villacorta; Sunit Talapatra; Foley & Lardner LLP

(57) ABSTRACT

The present invention relates to an image enhancing composition for the enhancement of contrast in a body cavity, wherein the viscosity of the composition is between 2000 and 4000 mPa·sec. It also relates to a method for enhancing contrast of an image of a body cavity, which method comprises introducing one single small amounts of an image enhancing composition into the body cavity. In another aspect, the present invention provides a high contrast image of a body cavity obtained by the method of the invention, in particular a 3-dimensional high contrast image.

14 Claims, 2 Drawing Sheets

COMPOSITION AND METHOD FOR MEDICAL IMAGING OR BODY CAVITIES

CROSS-REFERENCE TO RELATED PATENT APPLICATIONS

This application is a Divisional of U.S. application Ser. No. 11/632,364, filed Oct. 1, 2007 which is a National Stage of PCT/NL2005/000507, filed Jul. 14, 2005, which claims priority to European Application 04077057.0, filed Jul. 15, 2004. The contents of these applications are herein incorporated by reference in their entirety.

FIELD OF THE INVENTION

This invention relates to compositions and methods for medical imaging of the human or animal body. In particular to medical imaging with high contrast.

BACKGROUND OF THE INVENTION

Medical diagnostic imaging is widely used for the examination of body cavities. A prerequisite for the imaging of body cavities is the instillation of a fluid in order to obtain a fluid-filled cavity. In these fluid-filled cavities, the fluid has two functions (1) to open up the cavity from its "collapsed" state (distension) and (2) to enhance the contrast of the image of the body cavity. Conventionally, water or watery fluids are used for distension and contrast imaging. Sometimes, this is combined with the generation of bubbles, to further increase contrast. For example, U.S. Pat. No. 4,681,119 describes novel compositions and methods for generating microbubbles in a liquid-filled cavity for enhancing ultrasonic images of such cavities.

Since water easily leaks from the body cavity, it has to be replenished continuously during imaging. This is one of the big disadvantages of the use of water as a contrast medium during examination or imaging. This disadvantage may be solved partly by using liquid installation devices which reduce the leakage. For instance, a catheter equipped with an inflatable balloon may be used. However, this is not very convenient for the patient.

WO 03/094710 suggests a solid or semi-solid phase-shifting medium of pH 7.4 for providing contrast enhancement and/or distention of the subject body or organ cavity during imaging, radiographic visualisation or similar medical examinations. The medium is designed to have high, but undefined, viscosity initially and then to liquefy or lose viscosity after a period of time in order to facilitate easy removal of the medium from the body cavity. This phase-shifting medium includes polymers such as starches, and colloidal clays, such as bentonite and tragacanth, in order to achieve the phase shift. Disadvantage of such ingredients is that the additives, such as starches, will interfere with image formation.

WO 92/00707 describes an opthalmic gel suspension for dry eye application containing lightly cross-linked polymers of acrylic acid with a particle size of not more than 50 micrometer. These polymers are formulated with one or more opthalmic demulgents, such as cellulose derivatives, polyvinyl alcohol or polyvinylpyrrolidone, or opthalmic vasoconstrictors, and optionally with opthalmic adjuvants or additives, into gel suspensions. The opthalmic suspensions have a pH of about 6.6-8.0 and a viscosity of 500 to 4000 centipoise. Due to the acrylic acid polymers, these compositions will not be the preferred choice for imaging body cavities. In addition, the particles in these opthalmic gel suspension will interfere with image formation.

Therefore, there is a need for alternative contrast agents which do not easily leak from the body cavity during examination and which enable high quality images without jeopardising the safety of the patient.

SUMMARY OF THE INVENTION

It is an object of the present invention to provide an image enhancing composition for the enhancement of contrast in a body cavity, such as the uterine cavity, wherein the composition has a pH in the range of 5.5 to 7.5 and a viscosity in the range of 2000 to 4000 mPa·sec. when measured at room temperature. It is also an object of the present invention to provide a method for enhancing the contrast of an image of a body cavity, as well as to provide a high contrast image of a body cavity obtained by using said method.

DETAILED DESCRIPTION OF THE PREFERRED EMBODIMENTS

Figure 1C:
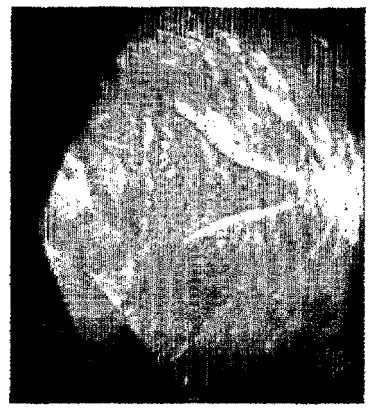
FIGS. 1a-1d
Illustrate a three dimensional picture of a uterus, wherein the picture was made using a gel composition according to the invention and a clear and sharp image without artifacts is obtained.
Figure 1D:
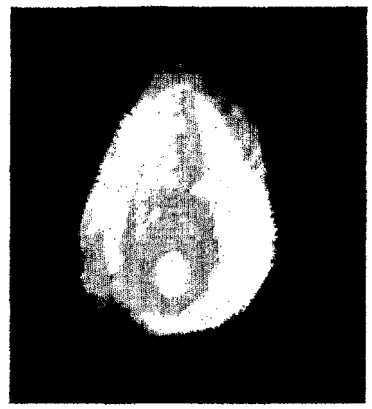
Figure 1A:
Figure 1B:
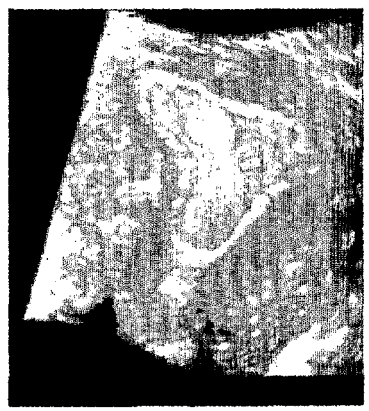
Figure 2:
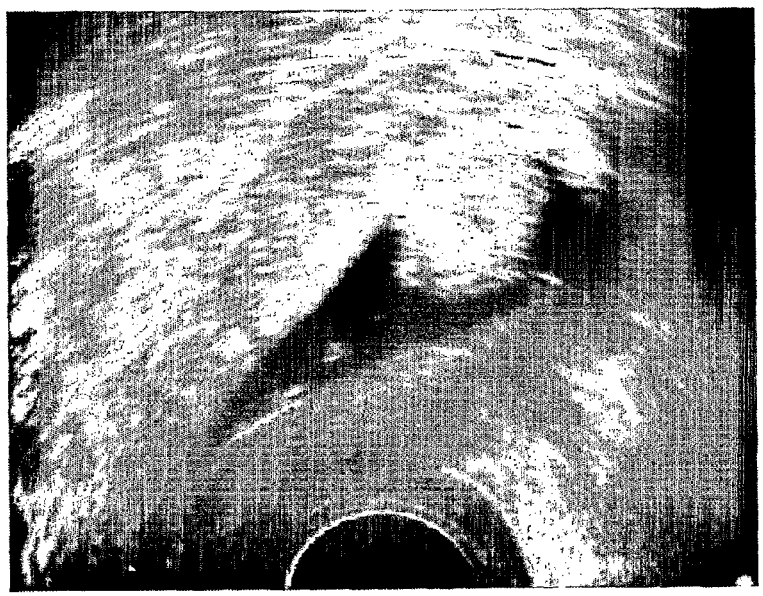
FIG. 2
Illustrates a two dimensional picture of a uterus, wherein the picture is made using conventional medium and three dimensional pictures are not possible with conventional medium because it would contain many artifacts due to a high flow of the medium.

The present invention relates to an image enhancing composition for the enhancement of contrast in a body cavity, wherein the viscosity of the composition is between 2000 and 4000 mPa·sec.

One of the advantages of the image enhancing compositions of the invention is that they overcome the inconveniences and discomfort caused by saline infusions. With these state of the art saline infusions fluid leakage frequently occurs if a catheter is used, or pain is experienced due to pressure of a balloon catheter.

Another advantage is that only small aliquots of the compositions according to the invention are needed to achieve an optimal distension of a body cavity.

Due to a much smaller leakage velocity in comparison to saline, examination of the cavity is possible for several minutes, even after removal of the installation device. Compositions of the invention have a viscosity of between 2000 and 4000 mPa·sec. as determined by standard viscosity determination methods, measured at room temperature and under atmospheric pressure. In one embodiment, the viscosity of the composition of the invention is between 2500 and 3500, preferably between 2700 and 3000 mPa·sec. More preferably, the viscosity of a composition of the invention is between 2800 and 2900 mPa·sec. when measured at room temperature. At body temperature the viscosity of a composition of the invention will be lower. Preferably, the viscosity will be between 2300 and 2500 mPa·sec. most preferably it will be between 2400 and 2500 mPa·sec. when measured at body temperature.

Image enhancing compositions of the invention may be used for all types of medical imaging, including X ray imaging, echography, magnetic resonance imaging, CT scanning and ultrasound imaging. Preferably, they are used for ultrasound imaging. More preferably, it is used for 3-dimensional ultrasound imaging.

As used herein, "image enhancement" refers to increasing the contrast of an image. The contrast enhancement may be either negative (black) or positive (white).

Typically, enhancement also involves distension of the body cavity of which an image is made. The compositions of the invention may be used for the imaging of any body cavity, including each part of the gastro-intestinal tract, such as the stomach, the colon. the duodenum; the bladder, the vagina. In a preferred embodiment, the body cavity is the uterine cavity.

Compositions of the invention should consist of substances which are safe for use in the human or animal body. They should be echo-lucent and the should therefore not contain particulate material, such as starch. Suitably, compositions of the invention are clear and do not contain particles, bubbles or protein, which will disturb the signal.

In one embodiment, the composition of the invention comprises a cellulose derivative, such as hydroxyethylcellulose or methylcellulose, in a buffer. Preferably, the composition comprises hydroxyethylcellulose. It is important that the composition contains so much of the cellulose derivative to achieve a viscosity of between 2000 and 4000 mPa·sec. as determined by standard viscosity determination methods, measured at room temperature and under atmospheric pressure, preferably between 2500 and 3500, or between 2700 and 3000 mPa·sec. More preferably, enough to achieve a viscosity of between 2800 and 2900 mPa·sec. when measured at room temperature. At body temperature, a viscosity of between 2300 and 2500 mPa·sec., most preferably of between 2400 and 2500 mPa·sec. should be achieved.

The skilled person will understand that adjuvants, such as disinfectants or a local anaesthetic, may be added, for instance glycerine, lidocaine and chlorohexidine. In addition contrast enhancers may be added, such as iodine for X-ray imaging. However, in a preferred embodiment of the invention the composition consists substantially of a cellulose derivative, such as hydroxyethylcellulose or methylcellulose in a buffer, and no other adjuvants such as alcohol, polyvidone, lidacoine, or related compounds.

The pH value of the composition is between about 5.5 and about 7.5. Preferably, between about pH 6.0 and about 7.0, more preferably between about pH 6.3 and about 6.8.

In another aspect, the compositions of the invention may be used to manufacture an image enhancing medium for use in a medical imaging procedure. The composition may advantageously be used in 3-dimensional imaging procedures. In one embodiment, the compositions of the invention are used in 3-dimensional sonohysterography. In another aspect, the invention provides for the use of an image enhancing composition according to the invention for enhancing contrast of an image of a body cavity. The method comprises introducing one single small aliquot of a medium comprising the composition of the invention in the body cavity. The skilled person will understand that the amount which has to be administered or introduced will be dependent on the size of the body cavity which has to be imaged. Typically, about 1-about 10 ml will be enough for most body cavities. In one embodiment, about 3-about 5 ml of an image enhancing composition according to the invention is used for ultrasonic examination of the uterine cavity. Constant infusion of the composition is not necessary, which is a great advantage of the method of the present invention.

A medium comprising a compositions of the invention may be administered or introduced in a body cavity by methods known in the art and depending on the body cavity which is to be examined. For instance, for examination of the uterus, the composition is typically administered via an instillation device, such as a catheter.

In yet another aspect, the invention provides for high contrast images which are obtainable by using the compositions of the invention. Also encompassed in the invention, are high contrast 3-dimensional images. In particular, high contrast 3-dimensional images of the bladder, gastro-intestinal tract and the uterus. In a preferred embodiment, the invention is used for so-called virtual hysteroscopy. Three dimensional imaging requires a very stable and quiet filling of the cavity of interest, with a minimum amount of artefacts. The gel and method of the invention enables this.

EXAMPLE

This example demonstrates how the compositions and method of the invention may effectively and safely be used for sonohysterography.

The composition used for sonohysterography was a sterile, clear viscous gel containing hydroxyethylcellulose, glycerin, lidocaine (2% w/w) and chlorohexidine (0.05% w/w) buffered with acetic acid.

The composition was instilled using a cheap and easy to handle instillation device developed with a back-flow valve and flexible cervical adaptation, preventing leakage of the gel to the vagina. However, state of the art installation devices may be used instead.

The ultrasonic properties of the gel appeared comparable to saline in the first 120 patients. With only about 4 ml already an optimal distension could be achieved (range 2-10 ml). The gel could therefore be instilled from a normal 10 ml syringe fixed to the device and carefully flushed prior to the instillation preventing the introduction of air bubbles. Due to a much slower leakage velocity as compared to saline, ultrasonographic examination of the uterine cavity was possible for a long time even after removal of the instillation device. Only in a few cases a quick collapse of the uterine cavity was seen directly after removal of the device. This also illustrated that there was hardly any leakage of the gel through the Fallopian tubes. Installation of the gel was less painful as compared to the introduction of a balloon catheter. This shows that gel instillation is an alternative for saline infusion and can be used effectively and safe for sonohysterography. Gel instillation sonohysterography offers a more stable filling of the uterine cavity allowing detailed examination without inconveniences.

The invention claimed is:

1. An echo-lucent image enhancing composition for the enhancement of contrast in a body cavity, wherein the composition comprises a cellulose derivative has a pH between 5.5 to 7.5 and a viscosity between 2000 to 4000 mPa·sec. when measured at room temperature wherein the composition is free of particulate matter that interfere with clear image formation.

2. The echo-lucent image enhancing composition according to claim 1, wherein the viscosity of the composition is between 2700 and 3000 mPa·sec, when measured at room temperature.

3. The echo-lucent image enhancing composition according to claim 1, wherein the composition is free of pyrrolidones, alcohols, disinfectants and anaesthetics.

4. The echo-lucent image enhancing composition according to claim 1, wherein the cellulose derivative is hydroxyethylcellulose or methylcellulose.

5. The echo-lucent image enhancing composition according to claim 1, wherein the composition provides enhancement of contrast in a uterine cavity.

6. The echo-lucent image enhancing composition according to claim 1, wherein the composition provides for three dimensional imaging.

7. A method for enhancing contrast of an image of a body cavity, comprising the step of introducing an echo-lucent image enhancing composition according to claim 1 into the body cavity.

8. The method according to claim 7, wherein the imaging is 3-dimensional imaging.

9. The method according to claim 7, wherein the imaging is an imaging procedure of the uterine cavity.

10. The method according to claim 9, wherein the imaging procedure comprises ultra-sound imaging.

11. A method for enhancing contrast of an image of a body cavity, comprising the step of introducing once 1-10 ml of an echo-lucent image enhancing composition according to claim 1 into the body cavity.

12. A high contrast image of a body cavity, wherein the high contrast image is a 3-dimensional image obtained by the method of claim 11.

13. The method according to claim 9, wherein the imaging procedure is sonohysterography.

14. A method for enhancing contrast of an image of a body cavity, comprising the step of introducing once 3-5 ml of an echo-lucent image enhancing composition according to claim 1 into the body cavity.

\* \* \* \* \*